(12) United States Patent
Khanna et al.

(10) Patent No.: US 8,343,200 B2
(45) Date of Patent: Jan. 1, 2013

(54) ORTHOPEDIC SCREW SYSTEM

(75) Inventors: A. Jay Khanna, Baltimore, MD (US);
Isador H. Lieberman, Cleveland, OH (US); Karthikeyan Ponnusamy, Ballwin, MO (US); Gaurav Gupta, McLean, VA (US); Sravisht Iyer, Naperville, IL (US); Alexander Hui, Bellavue, WA (US); Christopher Yu, Shreveport, LA (US); Kartik Trehan, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 1335 days.

(21) Appl. No.: 11/684,764

(22) Filed: Mar. 12, 2007

(65) Prior Publication Data
US 2007/0213732 A1    Sep. 13, 2007

Related U.S. Application Data

(60) Provisional application No. 60/782,069, filed on Mar. 13, 2006.

(51) Int. Cl.
*A61B 17/58* (2006.01)

(52) U.S. Cl. ...................................... 606/304

(58) Field of Classification Search .............. 606/65, 606/66, 70, 71, 280–299, 300–331; 411/372.5–377, 411/410–413
See application file for complete search history.

(56) References Cited

U.S. PATENT DOCUMENTS

| | | | |
|---|---|---|---|
| 4,640,271 A * | 2/1987 | Lower | 606/65 |
| 4,760,843 A * | 8/1988 | Fischer et al. | 606/304 |
| 5,569,251 A | 10/1996 | Baker | |
| 6,048,344 A * | 4/2000 | Schenk | 606/916 |
| 6,129,730 A | 10/2000 | Bono | |
| 6,187,008 B1 * | 2/2001 | Hamman | 606/318 |
| 6,214,012 B1 * | 4/2001 | Karpman et al. | 606/93 |
| 6,319,254 B1 * | 11/2001 | Giet et al. | 606/916 |
| 6,458,134 B1 * | 10/2002 | Songer et al. | 606/304 |
| 6,551,323 B2 | 4/2003 | Doubler | |
| 6,620,163 B1 * | 9/2003 | Michelson | 606/286 |
| 6,668,688 B2 * | 12/2003 | Zhao et al. | 81/439 |
| 6,726,691 B2 | 4/2004 | Osorio | |
| 7,582,107 B2 * | 9/2009 | Trail et al. | 606/304 |
| 2001/0049528 A1 * | 12/2001 | Kubota | 606/65 |
| 2004/0210227 A1 * | 10/2004 | Trail et al. | 606/73 |
| 2004/0243130 A1 | 12/2004 | Biscup | |
| 2005/0228385 A1 * | 10/2005 | Iott et al. | 606/61 |
| 2006/0036253 A1 | 2/2006 | Leroux | |

FOREIGN PATENT DOCUMENTS

JP    2003-24342 A    1/2003

* cited by examiner

*Primary Examiner* — Kevin T Truong
*Assistant Examiner* — Christopher Beccia
(74) *Attorney, Agent, or Firm* — PatentBest; Andrew McAleavey (57) ABSTRACT

An orthopedic screw system. The screw system comprises an outer member and an inner screw. The outer member has a longitudinal inner channel that defines an interior sidewall and is provided with screw threads on its exterior and interior sidewalls. An inner screw has threads constructed and arranged to engage with those on the interior sidewall, such that the inner screw may be secured within the inner channel. When secured within the inner channel, at least a portion of the length of the inner screw extends beyond the outer member. Methods of installing the orthopedic screw system into osteoporotic or otherwise weakened bone are also disclosed.

29 Claims, 11 Drawing Sheets

ORTHOPEDIC SCREW SYSTEM

CROSS-REFERENCE TO RELATED APPLICATIONS

This application claims the benefit of U.S. Provisional Patent Application No. 60/782,069, filed on Mar. 13, 2006. That application is incorporated by reference in its entirety.

BACKGROUND OF THE INVENTION

1. Field of the Invention

This invention relates to orthopedic screw systems used to fix surgical implants.

2. Description of Related Art

Orthopedic surgical implants, such as rods and plates, are often temporarily or permanently implanted in the body to repair fractures, and to gain fixation into bones to allow for the correction of various pathologies including deformity, instability and neoplastic conditions. Different types of implants have been created for different parts of the skeletal system and for different conditions. Regardless of type, most orthopedic implants have a common characteristic: they are anchored into bone by appropriate screws or other fasteners.

While the treatment of orthopedic conditions by implantation of orthopedic hardware is well established in patients with generally healthy bones, not all patients have healthy bones. If a bone screw is implanted in weakened or otherwise unhealthy bone, there is a greater risk that the bone screw will pull out or otherwise fail, in which case the implant secured by the bone screw may loosen, the orthopedic treatment may fail, and the patient may need more surgery to correct the problem.

Osteoporosis, a bone disease resulting in reduced bone mineral density and changes to the microstructure of the bones, is one of the major causes of weakened bones, although it is by no means the exclusive cause. At the time of writing, 20 million Americans suffer from osteoporosis, and 60 million are expected to suffer from it by the year 2020.

Osteoporosis can cause a number of different problems, including fractures of the hip and wrist and compression fractures of the vertebral column—the column of bones that encircles and protects the spinal cord. In particular, there are approximately 700,000 vertebral compression fractures in the United States per year.

Many of the problems associated with osteoporosis are themselves treatable. For example, compression fractures of the vertebrae are often treated with vertebral augmentation procedures, which are used to stabilize the spine. In a kyphoplasty, one type of vertebral augmentation procedure, the vertebral body is accessed through the vertebral pedicle, and catheters with balloons at their distal ends are inserted into the vertebral body. Once within the vertebral body, the balloons are inflated to create a cavity within the vertebral body, withdrawn, and bone cement is deposited into the cavity to fill it and, thus, to help restore the structural integrity of the vertebra and help treat the patient's pain. In another type of vertebral augmentation procedure, called a vertebroplasty, cement is injected into the vertebral body without first creating a cavity.

However, problems arise when a patient with weakened bones, due to osteoporosis, multiple myeloma, or some other condition, also has a diagnosis, such as scoliosis, infection, tumor, or degenerative stenosis, which would typically necessitate the implantation of orthopedic hardware. In those cases, many surgeons are reticent to implant corrective orthopedic hardware because of the increased risk of bone screw pull-out and instrumentation failure.

Therefore, it would be advantageous to have bone screws and surgical techniques that lower the risk of pull-out in patients with weakened bones.

SUMMARY OF THE INVENTION

One aspect of the invention relates to an orthopedic screw system. The system comprises an elongate outer member and an elongate inner screw. The outer member has an exterior sidewall, a first end, a second end opposite the first end, and a longitudinal inner channel that extends between and is open at the first and second ends, the inner channel defining an interior sidewall. The exterior and interior sidewalls of the outer member are provided with screw threads. The screw threads of the exterior sidewall are adapted to engage bone. The inner screw has a shaft with a first shaft end proximate and a second shaft end opposite the first shaft end. The shaft includes screw threads along substantially the entirety of its length constructed and adapted to engage the screw threads of the interior sidewall of the outer member so as to bring the outer member and the inner screw into engagement. The outer member and the inner screw are sized and proportioned relative to one another such that in an operative position, at least about 30% of the length of the inner screw extends beyond the second end of the outer member when the inner screw and the outer member are fully engaged with one another.

Another aspect of the invention relates to a pedicle screw system. The pedicle screw system comprises a generally cylindrical outer member and an elongate inner screw. The outer member has a first end, a second end, an exterior circumferential surface with a set of outer screw threads, and a generally longitudinal, generally cylindrical inner channel with a set of screw threads. The outer screw threads are constructed and arranged to engage at least a portion of the pedicle of a vertebra so as to secure the outer member in a fixed position within the pedicle of a vertebra oriented such that the second end of the outer member is oriented toward the vertebral body of the vertebra. The inner channel of the outer member has sufficient diameter to act as a passageway for surgical instruments. The inner screw has a shaft. The shaft has a first shaft end and a second shaft end opposite the first shaft end. Screw threads are formed on the exterior of the shaft. The screw threads on the exterior of the shaft are constructed and arranged to engage with the inner screw threads of the outer member so as to bring the inner screw into engagement with the outer member when the inner screw is within the inner channel of the outer member. The outer member and the inner screw are sized and proportioned relative to one another such that when they are in an operative position with the inner screw within the inner channel of the outer member, at least 30% of the length of the inner screw extends beyond the second end of the outer member when the outer member and the inner screw are fully engaged with one another and, with the outer member in the fixed position within the pedicle of the vertebra, at least the inner screw extends into the vertebral body of the vertebra.

Yet another aspect of the invention relates to a method of performing a vertebral augmentation procedure with pedicle screw insertion. The method comprises placing an outer member such that at least a portion of the outer member is within the pedicle of a vertebra. The outer member has an exterior sidewall, a first end, a second end opposite the first end, and a longitudinal inner channel that extends between and is open at the first and second ends. The longitudinal inner channel defines an interior sidewall. The exterior and interior sidewalls of the outer member are provided with screw threads. The screw threads on the exterior sidewall engage the vertebral pedicle to secure the outer member. The method further comprises directing bone cement into the vertebral body of the vertebra using the inner channel in the outer member and placing an inner screw within the inner channel such that screw threads of the inner screw engage with the screw threads of the interior sidewall. When the inner screw and outer member are in full engagement, at least about 30% of the length of the inner screw extends beyond the second end of the outer member, with at least a portion of the length of the inner screw extending into the bone cement.

Yet another aspect of the invention relates to an orthopedic screw system. The system comprises an elongate outer member and an elongate inner screw. The outer member has an exterior sidewall, a first end, a second end opposite the first end, and a longitudinal inner channel that extends between and is open at the first and second ends, the inner channel defining an interior sidewall. The exterior and interior sidewalls of the outer member are provided with screw threads. The screw threads of the exterior sidewall are adapted to engage bone. The outer diameter of the outer member decreases from the first end toward the second end. The inner screw has a shaft with a first shaft end and a second shaft end opposite the first shaft end. The shaft includes screw threads along substantially the entirety of its length constructed and adapted to engage the screw threads of the interior sidewall of the outer member so as to bring the outer member and the inner screw into engagement. The screw threads increase in width from the first shaft end toward the second shaft end. The outer member and the inner screw are sized and proportioned relative to one another such that in an operative position, at least a portion of the length of the inner screw extends beyond the second end of the outer member when the inner screw and the outer member are fully engaged with one another.

A further aspect of the invention relates to a method of performing orthopedic surgery. The method comprises fixing an outer member in a bone and securing an inner screw within the outer member such that screw threads of the inner screw engage with screw threads of an interior sidewall of the outer member. When the inner screw and the outer member are fully engaged, at least about 30% of the length of the inner screw extends beyond the second end of the outer member.

Yet another further aspect of the invention relates to a method of fixing an orthopedic screw into weakened bone. The method comprises fixing an outer member, at least in part, into cortical bone, such that a first end of the outer member is fixed proximate to an outer surface of the weakened bone, depositing bone cement into the weakened bone through an inner channel in the outer member and securing an inner screw within the outer member. When the inner screw and the outer member are fully engaged, at least a portion of the length of the inner screw extends beyond the second end of the outer member and into surrounding structure.

These and other aspects, features, and advantages of the invention will be set forth in more detail in the description that follows.

BRIEF DESCRIPTION OF THE DRAWINGS

The invention will be described with respect to the following drawing figures, in which like numerals represent like features throughout the figures, and in which.

DETAILED DESCRIPTION

Figure 1:
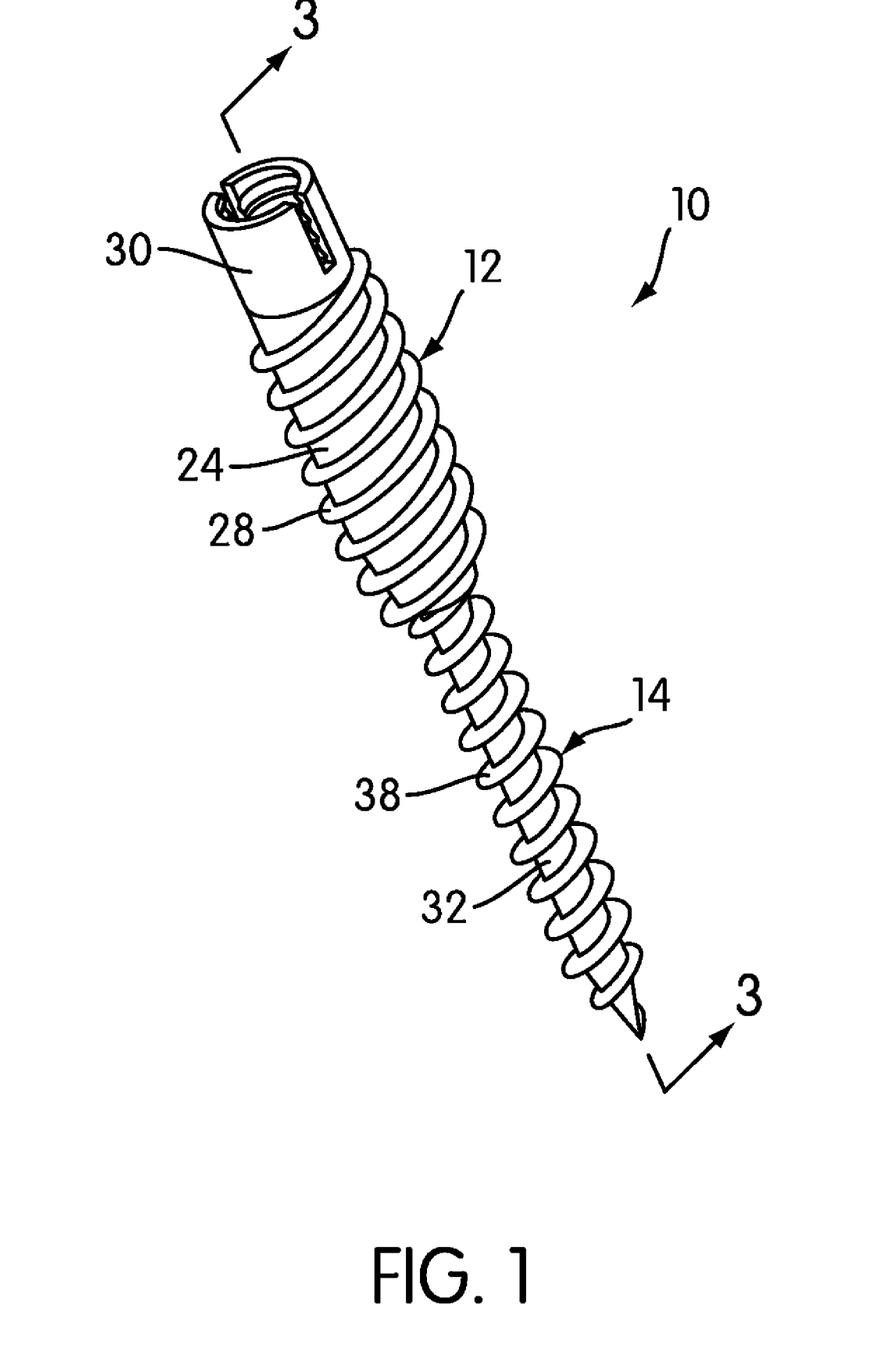
FIG. 1 is a perspective view of an orthopedic screw system, showing the outer member and the inner screw of the screw system in engagement.
Figure 2:
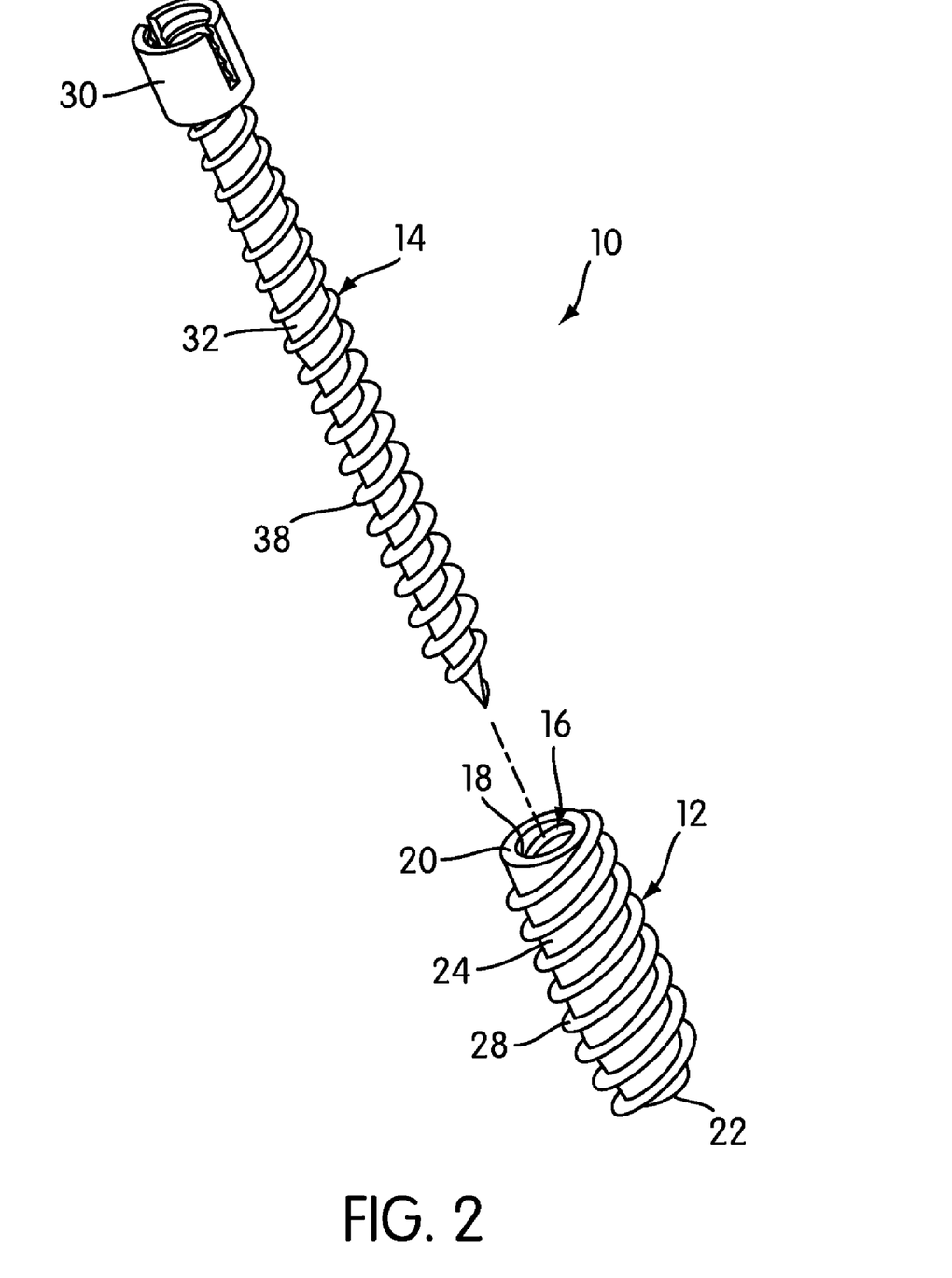
FIG. 2 is an exploded perspective view of the orthopedic screw system of FIG. 1.
Figure 3:
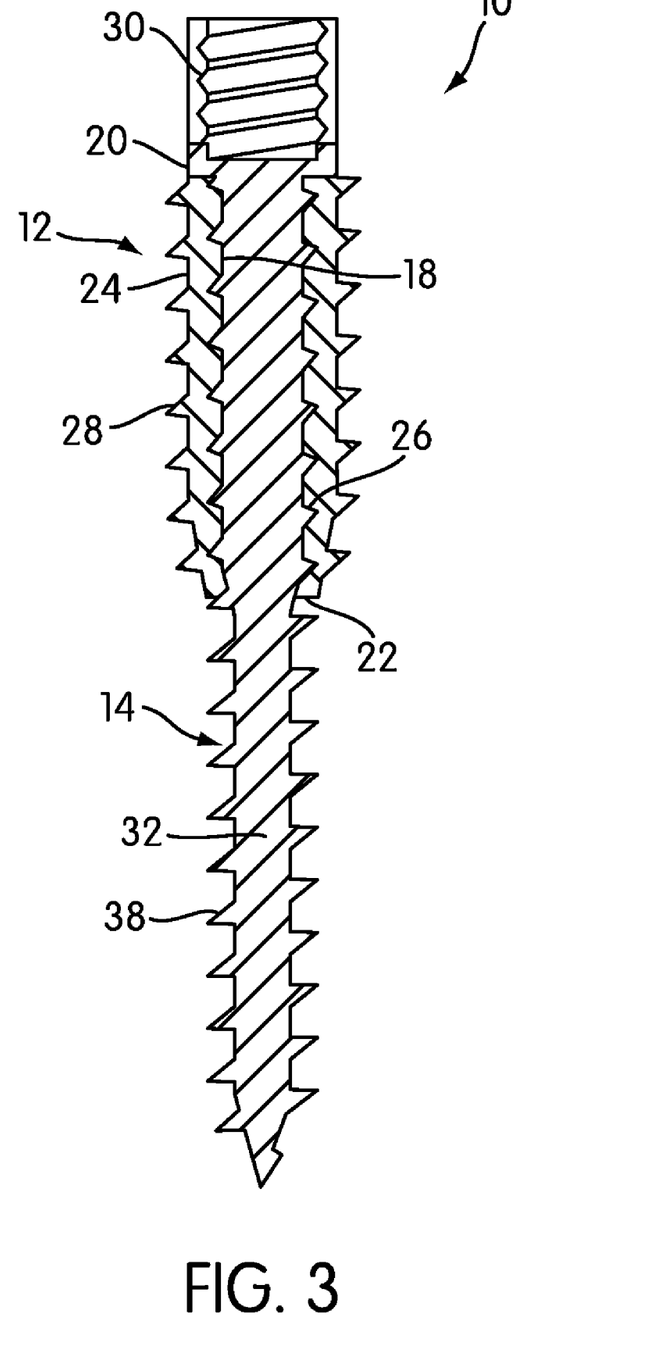
FIG. 3 is a cross-sectional view of the orthopedic screw system of FIG. 1 in engagement taken through Line 3-3 of FIG. 1.

FIG. 1 is a perspective view of an orthopedic screw system, generally indicated at 10. The orthopedic screw system 10 includes two elements: an outer member 12 and an inner screw 14. In FIG. 1, the outer member 12 and inner screw 14 are secured together in their fully engaged position; FIG. 2 illustrates the two components 12, 14 separately in an exploded perspective view, and FIG. 3 is a cross-sectional view, taken through Line 3-3 of FIG. 1, of the two components 12, 14 in their fully engaged position.

In some embodiments, the orthopedic screw system 10 may be used as a pedicle screw system for implantation into vertebrae, and some aspects of the following description may focus on or explain the suitability of the orthopedic screw system 10 for that purpose. However, the orthopedic screw system 10 may be used for any application, and in any surgical procedure, in which its features would be advantageous.

The outer member 12 of the orthopedic screw system 10 is an elongate, generally cylindrical component. Formed longitudinally through its center is a generally cylindrical inner channel 16 that is open at both the top face 20 and the bottom face 22 of the outer member 12. The inner channel 16 defines an interior sidewall 18 of the outer member 12. Both the interior and exterior sidewalls 18, 24 of the outer member 12 are provided with screw threads 26, 28. The screw threads 26, 28 extend over substantially the entirety of the length of the outer member 12. As will be described below in greater detail, the screw threads 28 of the exterior sidewall 24 are constructed and adapted to engage and fix the outer member 12 within bone, while the screw threads of the interior sidewall 18 are constructed and adapted to engage the inner screw 14.

Thus, the outer member 12 has the overall shape of a relatively short cylindrical tube, threaded on the interior and exterior. Additionally, as shown in FIGS. 1-3, the distal portion of the outer member 12 (i.e., the portion of the outer member 12 proximate to its bottom face 22) is tapered. More particularly, approximately the distal one-fourth of the outer member 12 is tapered. However, the distal taper of the outer member 12 is an optional feature. In some embodiments, the diameter of the outer member 12 may decrease without a taper; in other embodiments, the diameter of the outer member 12 may be substantially constant.

The inner screw 14 has a head 30 and a shaft 32. The head 30 of the inner screw is constructed and adapted to engage and secure orthopedic hardware, and may have any shape, size, profile, or features known in the art for that purpose. As examples of head configurations, U.S. Patent Application Publication No. 2006/0036253 to Leroux et al. and U.S. Patent Application Publication No. 2004/0243130 to Biscup et al. disclose and cite various screw head mechanisms, and are incorporated by reference to the extent that they disclose those screw head mechanisms. The head 30 of the inner screw 14 is shown in FIGS. 1-3 as a fixed angle head, although other embodiments of the inner screw with variable angle heads (also known as polyaxial heads) will be described below.

The shaft 32 of the inner screw 14 has a first or top end 34 that terminates at the head 30, a second or lower end 36 opposite the first end 34, and screw threads 38 that cover substantially the entirety of the length of the shaft 32 between the first and second ends 34, 36. The shaft 32 is of a size such that the inner screw 14 will fit within the inner channel 16 of the outer member 12 with the screw threads 26 of the interior sidewall 18 engaging the screw threads 38 of the shaft 32 to bring the inner screw 14 into engagement with the outer member 12. In most embodiments, the pitch of the engaging screw threads 26, 38 may be relatively fine and selected so as to provide a tight fit with very little "slack" or "play."

As can be seen in FIGS. 1-3, the outer member 12 and the inner screw 14 are sized and proportioned relative to one another such that the inner screw 14 is longer than the outer member 12 and, when the outer member 12 and the inner screw 14 are fully engaged, the inner screw 14 extends beyond the bottom face 22 of the outer member 12. Generally speaking, about 30% to about 60% of the length of the inner screw 14 may extend beyond the outer member 12 when the outer member 12 and the inner screw 14 are fully engaged. That allows both the outer member 12 and the inner screw 14 to be anchored independently in a different part of the bone, so that each component 12, 14 contributes to the fixation of the orthopedic screw system 10 as a whole and the two components 12, 14 are essentially mutually reinforcing when fully engaged. For example, the outer member 12 could be fixed, at least in part, in cortical bone, and the distal length of the inner screw 14 that extends beyond the outer member 12 could be fixed in cancellous bone. With each component independently anchored in the bone, the failure of the bone or the device/bone interface proximate to one of the components 12, 14 may not necessarily result in pull-out of the entire orthopedic screw system 10.

The inner screw 14 may also include a number of other features. For example, in the illustrated embodiment, the shaft 32 of the inner screw 14 begins a gradual taper to a smaller diameter beyond the bottom face 22 of the outer member 12. (In other embodiments, the diameter may be decreased without a taper, or there may be no decrease in diameter.) However, as the diameter of the shaft 32 decreases, the width of the screw threads 38 on the shaft 32 increases, such that the inner screw 14 as a whole maintains a constant diameter from the top to the bottom. The increased width of the screw threads 38 in the distal portion of the shaft 32 may help to anchor the inner screw 14 in lower-density (osteoporotic or osteopenic) or weakened bone.

The precise size and proportions of the outer member 12 and inner screw 14 relative to one another may vary, depending on the application, the size and gender of the patient in which they are to be used, and the morphology of the bone structures within that patient. As an example, if the orthopedic screw system 10 is used as a pedicle screw system, the entire screw system may have a length in the range of about 30 mm to about 60 mm, with the outer member 12 having a length in the range of about 15 mm to about 30 mm. If used as a pedicle screw, it is advantageous if the length of the outer member 12 is chosen so as to extend beyond the neural canal in the vertebra when in its operative position. A length of 25 mm may be suitable for that purpose. The outer member 12 may have an inner channel 16 with a diameter of 4 mm and 0.5 mm screw threads 26. The screw threads 28 on the exterior sidewall 24 of the outer member 12 may be about 1 mm in width. Thus, the total exterior diameter of the outer member 12 (and of the orthopedic screw system 10 as a whole) may be about 7 mm, including the diameter of the inner channel 16, the wall thickness between the interior and exterior sidewalls 18, 24, and the exterior screw threads 28. As with conventional pedicle screws that are currently used, the orthopedic screw system 10 may have sizes ranging from approximately 5.0 mm to 9.0 mm in diameter.

The inner screw 14 generally has a diameter and screw thread 38 width sized and adapted to mate with the inner channel 16 of the outer member 12, as was described above. (Given the above dimensions for the inner channel 16, the diameter of the inner screw 14 may be approximately 4 mm in total.) Beyond the bottom face 22 of the outer member 12, the shaft 32 may taper significantly, for example, to a diameter of 2 mm as the screw threads 38 increase in width to 1 mm, thus maintaining the overall 4 mm diameter of the inner screw 14.

The screw thread pitch or pitches used for the various screw threads 26, 28, 38 may be the same or different, and may range from about 1.8 mm to about 3.2 mm. In some embodiments, for example, all of the screw threads 26, 28, 38 may have a pitch of 3 mm. Additional embodiments of the orthopedic screw system 10 will be described below in greater detail.

The outer member 12 and inner screw 14 are most advantageously made of a strong, biocompatible material, and both components 12, 14 are most advantageously made of the same material. Biocompatible metals are particularly suitable for the outer member 12 and the inner screw 14. Examples of suitable biocompatible metals include stainless steels, such as 316L stainless steel, 316LVM stainless steel, 22Cr-13Ni-5Mn stainless steel; titanium; and titanium alloys, such as Ti-6Al-4V titanium alloy. In some embodiments, other biocompatible materials, including plastic and composite biocompatible materials, may be used. Any suitable method of formation may be chosen, including molding, casting, machining, and other techniques.

The orthopedic screw system 10 may be particularly useful in the process of implanting orthopedic hardware and anchoring it in weakened bone, for example, when implanting orthopedic hardware in a patient with osteoporosis. In those cases, the actual implantation of the orthopedic screw system 10 may be advantageously combined with procedures to stabilize and restore integrity to the weakened bones into which the orthopedic screw system 10 is being implanted. The description below will focus on an example of the use of the orthopedic screw system 10 as a pedicle screw in a case where the vertebra into which it is to be implanted has suffered a compression fracture or has otherwise become unstable. As will be described below in more detail, in order to implant the orthopedic screw system 10 and reduce the likelihood of screw pull-out, the implantation of the orthopedic screw system 10 is combined with tasks from a vertebral augmentation.

Figure 4:
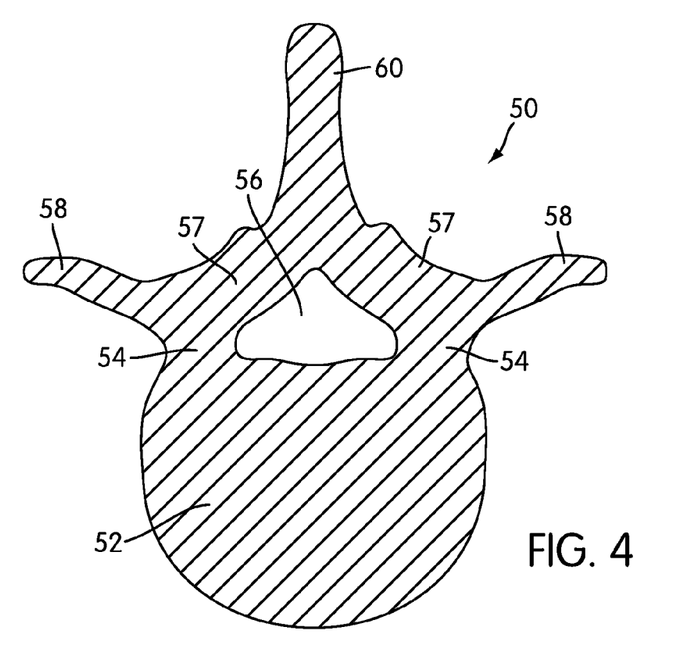
FIG. 4 is a horizontal cross-sectional view of an exemplary vertebra, illustrating the anatomy relevant to a vertebral augmentation procedure.

FIG. 4 is a cross-sectional view of a vertebra 50, which may be assumed to be the second lumbar (L2) vertebra. However, as those of skill in the art will realize, vertebral anatomy of different vertebrae is generally similar, and the methods described below may be readily adapted for use on other vertebrae.

The vertebra 50 has a vertebral body 52, on which the intervertebral disk (not shown in FIG. 4) rests. The pedicles 54 extend outward from the back of the vertebral body 52 and define the side portions of the spinal canal 56, through which the spinal cord and other neural elements pass. The laminae 57 complete the spinal canal 56 posterior of the vertebral body 52 and support the various processes that extend from it. Joining the pedicles 54 and extending generally laterally outward from them to are two transverse processes 58. Extending directly posterior, from the junction of the two laminae 57, is the spinous process 60. Between the transverse processes 58 and the spinous process 60, the superior and inferior articular processes (not shown in FIG. 4) extend above and below the plane of the vertebral body 52 to form the superior and inferior facet joints with the adjacent L1 and L3 vertebrae.

Figure 5:
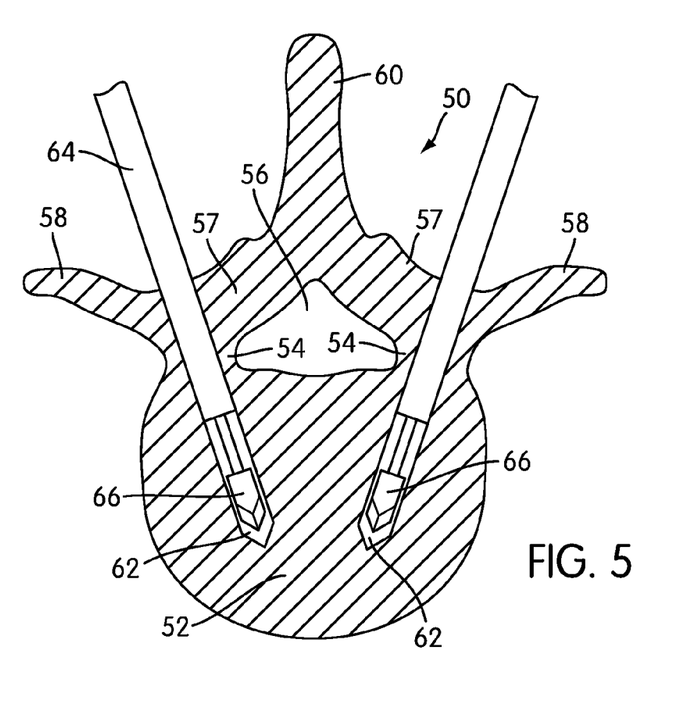
FIGS. 5-10 are horizontal cross-sectional views of the vertebra of FIG. 4, illustrating the steps of a vertebral augmentation procedure and screw implantation procedure using the orthopedic screw system of FIG. 1.

FIG. 5 illustrates a first task in the stabilization of the vertebra 50 and the implantation of the pedicle screw system 10. The task illustrated in FIG. 5 assumes that the patient has been prepared for surgery in the usual fashion, and that any preparatory tasks that might be indicated have been performed. Moreover, the description of a basic method that follows may be modified by the surgeon at his or her discretion to add additional tasks when the patient's condition or other factors warrant.

As shown in FIG. 5, the first task in the method is the creation of holes that extend from the pedicles 54 into the vertebral body 52. These holes 62 are made at the conventional insertion point for pedicle screws, which is near the junction of the transverse process 58 and the facet joint. The angle of insertion roughly matches the angle of the pedicles 54 so that the holes 62 will extend into the vertebral body 52 through the pedicles 54. As shown in FIG. 5, the holes 62 are typically made by inserting a cannula 64 with a trocar 66 (a tool with a punch or blade at its leading edge) and exerting appropriate force. Of course, other techniques and tools are capable of creating the holes 62 and may be used. For example, in some embodiments, a drill may be used to expand or bore out the holes 62 after the trocar 66 is withdrawn from the cannula 64. In some embodiments, a tool known as a "gear shift" may be used to make the holes 62. The precise manner in which the holes 62 are made is not critical, so long as the position and extent of the holes 62 is appropriate for the patient and the procedure when the task is complete.

Figure 6:
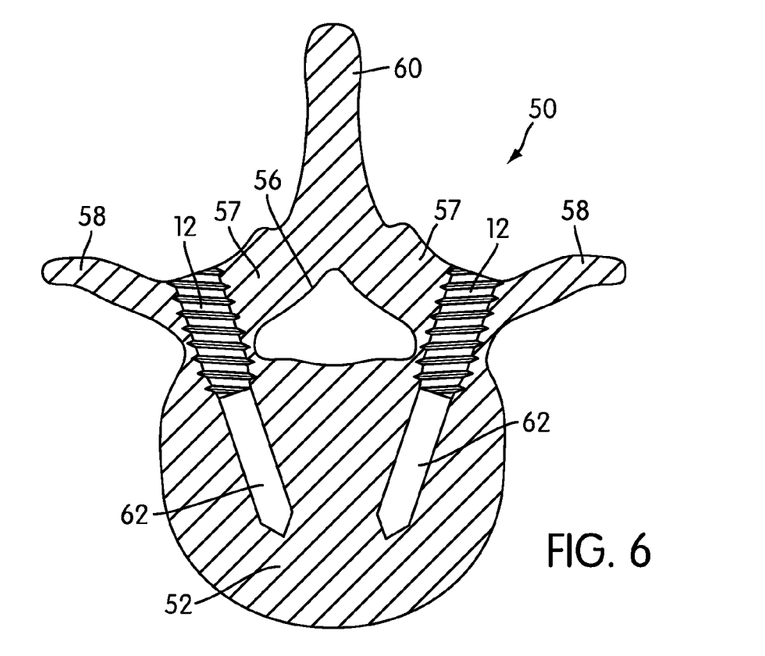

FIG. 6 illustrates the next task in the method. Once the holes 62 have been formed, an outer member 12 is secured within each hole 62, such that the screw threads 28 of the exterior sidewall 24 engage the surrounding bone to anchor the outer members 12 substantially within the pedicles 54. The bottom face 22 of the outer member 12 extends beyond the spinal canal 56, a feature that may increase the safety of the system 10, because nothing inserted into or through the outer member 12 can break into the spinal canal 56 or affect the spinal canal 56 as a whole.

In FIG. 6, two outer members 12 are shown in their final positions within the pedicles 54. In practice, the outer members 12 may be advanced into those positions in essentially the same way that a conventional pedicle screw is placed. In some embodiments, the outer members 12 may be advanced driven into the positions illustrated in FIG. 6 alone, while in other embodiments, the surgeon may advance the entire system 10, including the inner screw 14, and then remove the inner screw 14 to leave the outer members 12 in the position illustrated in FIG. 6. Ultimately, the precise manner in which the outer members 12 are installed, and the tools used to install them, are not critical, so long as the installed outer members 12 have essentially the positions shown in FIG. 6. The bottom faces 22 of the outer members 12 may extend as far as the posterior one-third of the vertebral body 52.

One particular advantage of the system 10 is that once the outer members 12 are installed in the positions shown in FIG. 6, their inner channels 16 can themselves be used as cannulas to access the vertebral body 52. Thus, access for the remaining tasks of the method is established and, as indicated above, it is more likely that instruments inserted through the inner channels 16 of the outer members 12 will be inserted along the correct line of action and to the correct position.

Once the outer members 12 are installed, the method continues with the some of the tasks of a traditional vertebral augmentation procedure. In particular, FIGS. 7-10 illustrate a kyphoplasty procedure, but a vertebroplasty procedure or another form of vertebral augmentation procedure may be performed.

Figure 7:
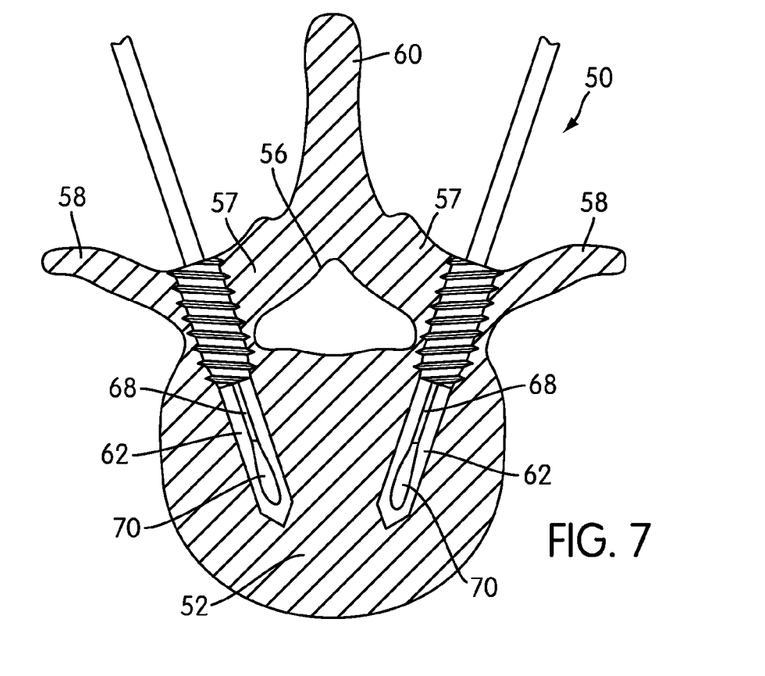
Figure 8:
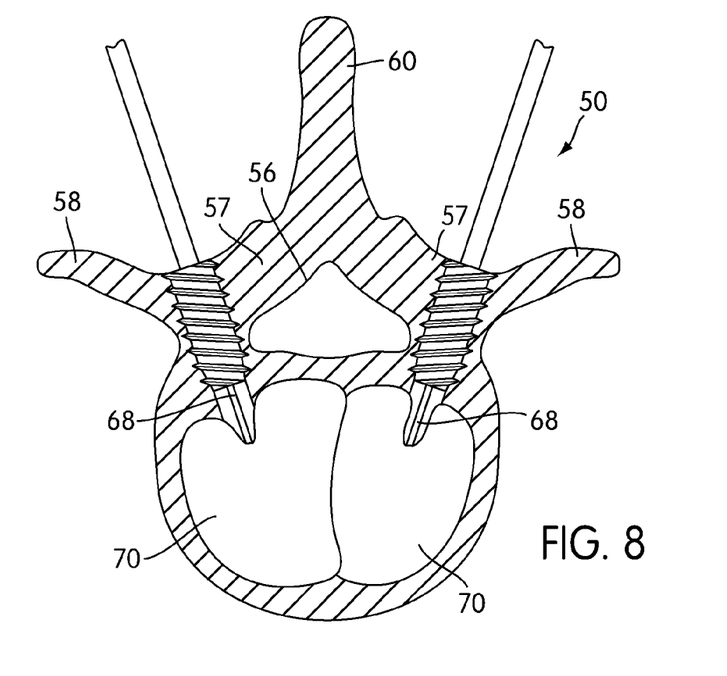

As shown in FIG. 7, two balloon catheters (also known as inflatable balloon tamps) 68 are inserted into the holes 62 through the respective inner channels 16 of the outer members 12. Once properly positioned in the vertebral body 52, the balloons 70 of the balloon catheters are inflated to create a cavity 72 in the vertebral body 52, as shown in FIG. 8. After the cavity 72 has been created, the balloons 70 are deflated and the balloon catheters 68 are withdrawn.

Figure 9:
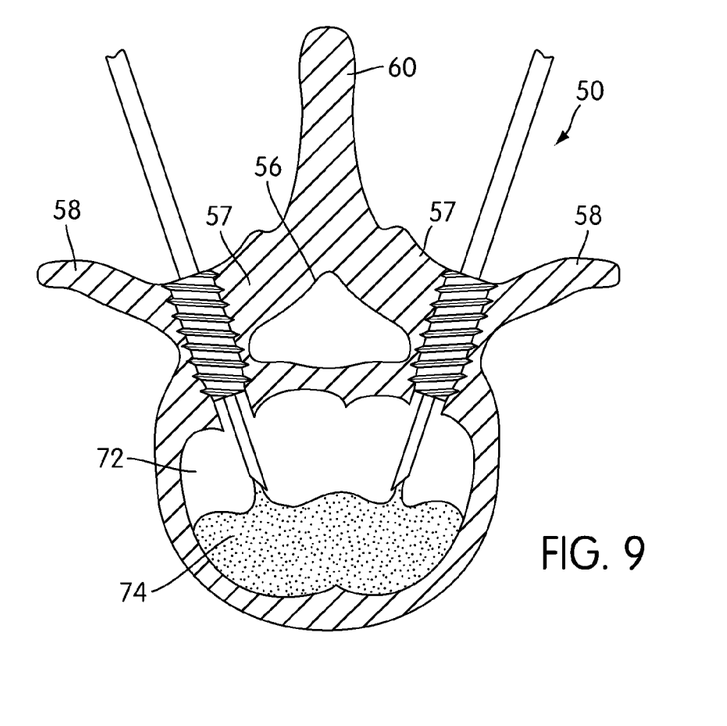

Next, bone cement 74 is deposited into the cavity 72 in the vertebral body 52 in an anterior-to-posterior direction. The bone cement that is used may be any suitable bone cement. Poly(methyl methacrylate) (PMMA) bone cement is suitable, and any other conventional bone cement or material suitable for the purpose may also be used. The bone cement would be mixed to a conventional viscosity and deposited at a conventional rate.

Figure 10:
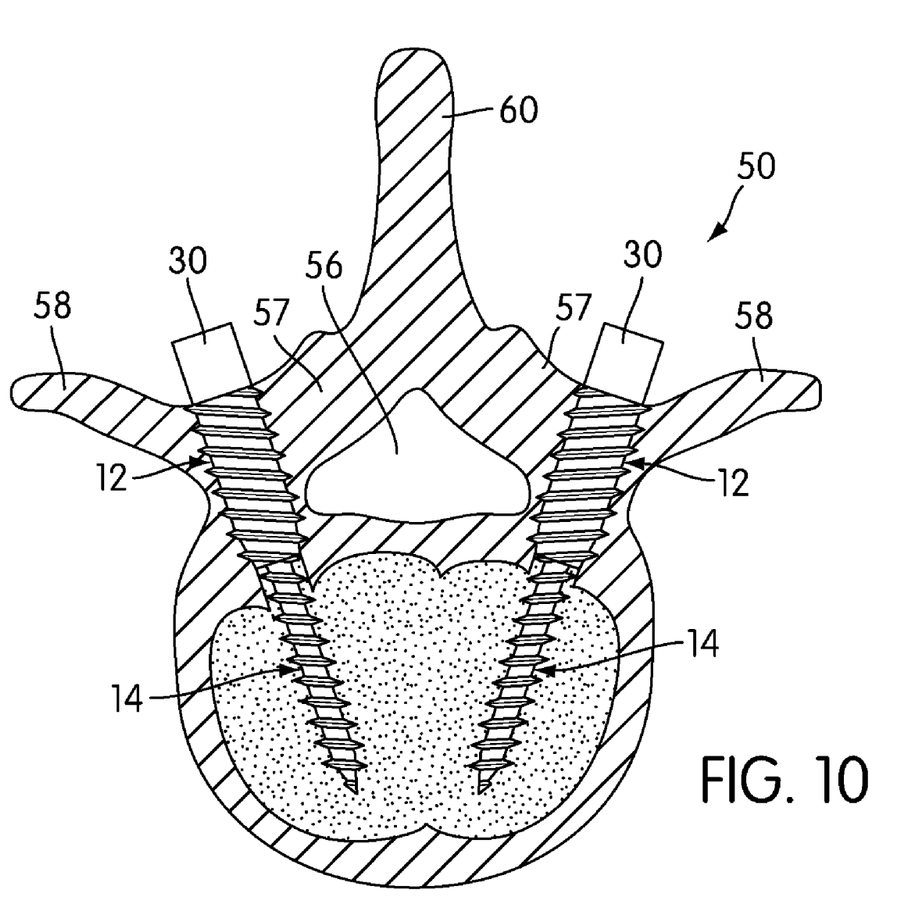

Finally, as shown in FIG. 10, preferably before the bone cement 74 is completely hardened and cured, the inner screw 14 is inserted into and brought into engagement with the outer member 12. Because the outer member 12 is already positioned at the correct angle and defines at least a part of the insertion path, it may be easier to insert the inner screw 14 and avoid any "fumbling" or misplacement of the inner screw 14. In the position shown in FIG. 10, the distal portion of the inner screw 14 is fixed within the curing bone cement 74 that was previously deposited in the vertebral body 52. Once the inner screws 14 have been inserted, orthopedic hardware can be fastened to their heads 30 in any conventional manner.

In the position illustrated in FIG. 10, with the outer member 12 implanted largely in cortical bone and the inner screw 14 fixed in cancellous bone and bone cement, the two components 12, 14 are in the mutually reinforcing position described above, such that the pull-out strength of the orthopedic screw system 10 may be greater than that of a conventional bone screw placed into weakened or osteoporotic bone.

If the method illustrated in FIGS. 5-10 were to be modified for a vertebroplasty, it would be performed essentially in the same manner, except that no cavity 72 would be formed—the bone cement 74 would simply be injected directly into the vertebral body 52.

Figure 11:
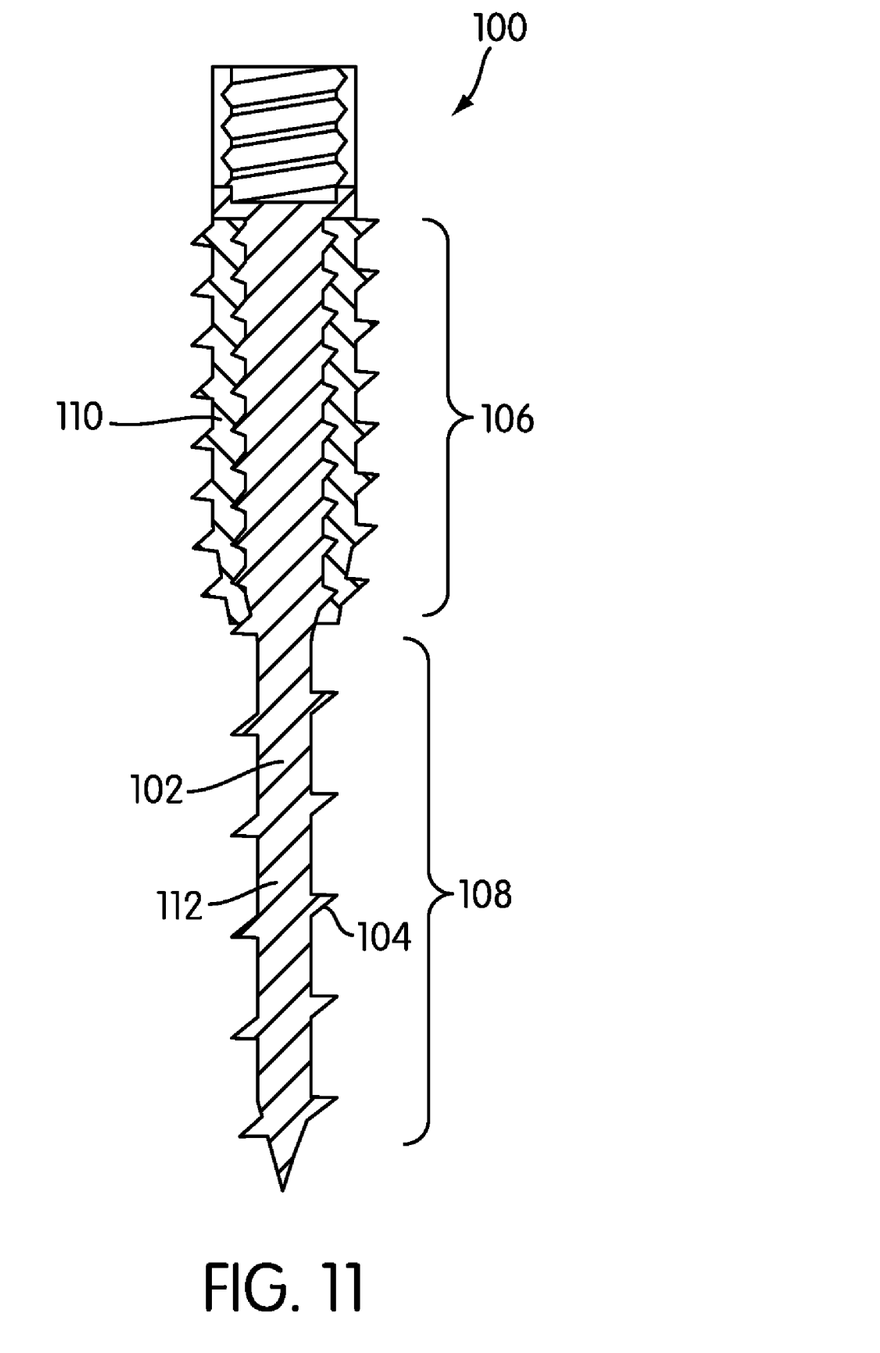
FIG. 11 is a cross-sectional view of an orthopedic screw system according to another embodiment of the invention, illustrating an inner screw with a finer thread pitch on an upper portion thereof and a coarser thread pitch on a lower portion thereof.

As was noted above, certain modifications may be made to the orthopedic screw system 10 in some embodiments. For example, FIG. 11 is a cross-sectional view of another embodiment of an orthopedic screw system 100. The orthopedic screw system 100 is generally similar to the orthopedic screw system 10; therefore, the description above will suffice for those components not described here.

The primary difference between the orthopedic screw system 10 and the orthopedic screw system 100 is that the inner screw 102 of the orthopedic screw system 100 is that the screw threads 104 of the inner screw 102 have two distinct pitches. In the proximal portion 106 of the inner screw 102, the screw threads 104 have a relatively fine pitch, so as to establish the tight fit between the inner screw 102 and the outer member 110 that was described above; in the distal portion 108, the screw threads 104 have a coarser pitch, so as to gain better purchase in bone or bone cement. Any screw thread pitches within the range described above may be used. Additionally, in order to facilitate insertion of the inner screw 102 into the outer member 110 and to avoid any interference or "jamming" that might be caused by the different thread pitches, the screw threads in the coarser distal portion 108 may be made with a very slightly reduced width or the shaft 112 may be tapered slightly more in that region so that the inner screw 102 can be inserted easily into the outer member 110.

Figure 12:
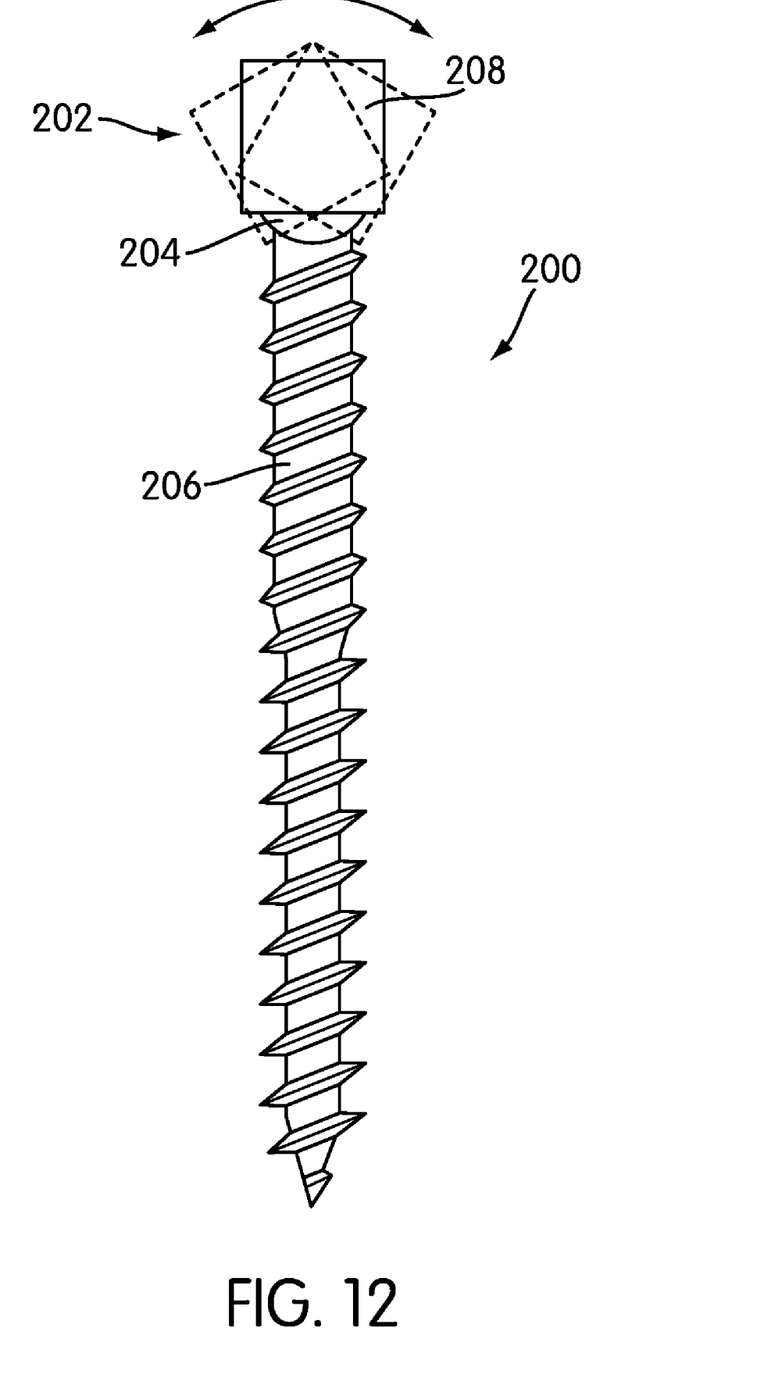
FIG. 12 is a side elevational view of an orthopedic screw system according to another embodiment of the invention, illustrating an inner screw with a variable angle head.

As was described above, the inner screw 14 can have any sort of head 30 that facilitates attachment to orthopedic hardware. The head 30 of the inner screw 14 is a fixed angle head, but embodiments of orthopedic screw system 10 may, and often will, use variable angle (also known as polyaxial) heads. FIG. 12 is a side elevational view of another embodiment of an inner screw 200, which is generally similar to the inner screw 14. The inner screw 200, however, includes a variable angle head 202. This example of a variable angle head 202 includes a ball portion 204, which is fixed to the shaft 206 of the inner screw 200, and a movable segment 208.

Figure 13:
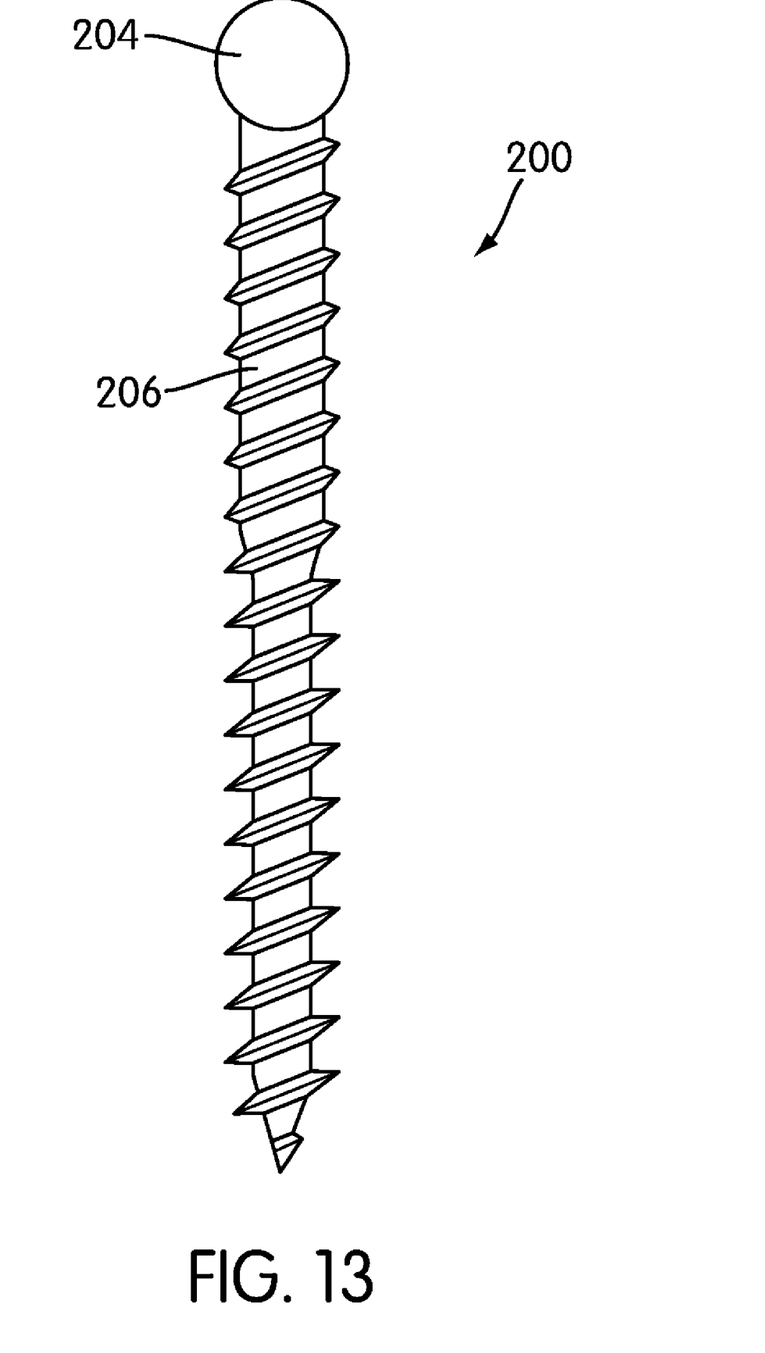
FIG. 13 is a side elevational view of an inner screw of an orthopedic screw system with a generic ball head, according to another embodiment of the invention.

Some embodiments of the invention may be made with a generic ball portion 204 acting as the head of the inner screw 14, 200. FIG. 13 is a side elevational view of the inner screw 200 showing the ball portion 204. The other components of a variable angle head may then be attached to the ball portion 204 as a later step in manufacturing, or after the component is distributed. In some embodiments, the ball portion 204 may be separable and attached to the inner screw 200 only after it is implanted, in order to provide surgeons with maximum flexibility.

Figure 14:
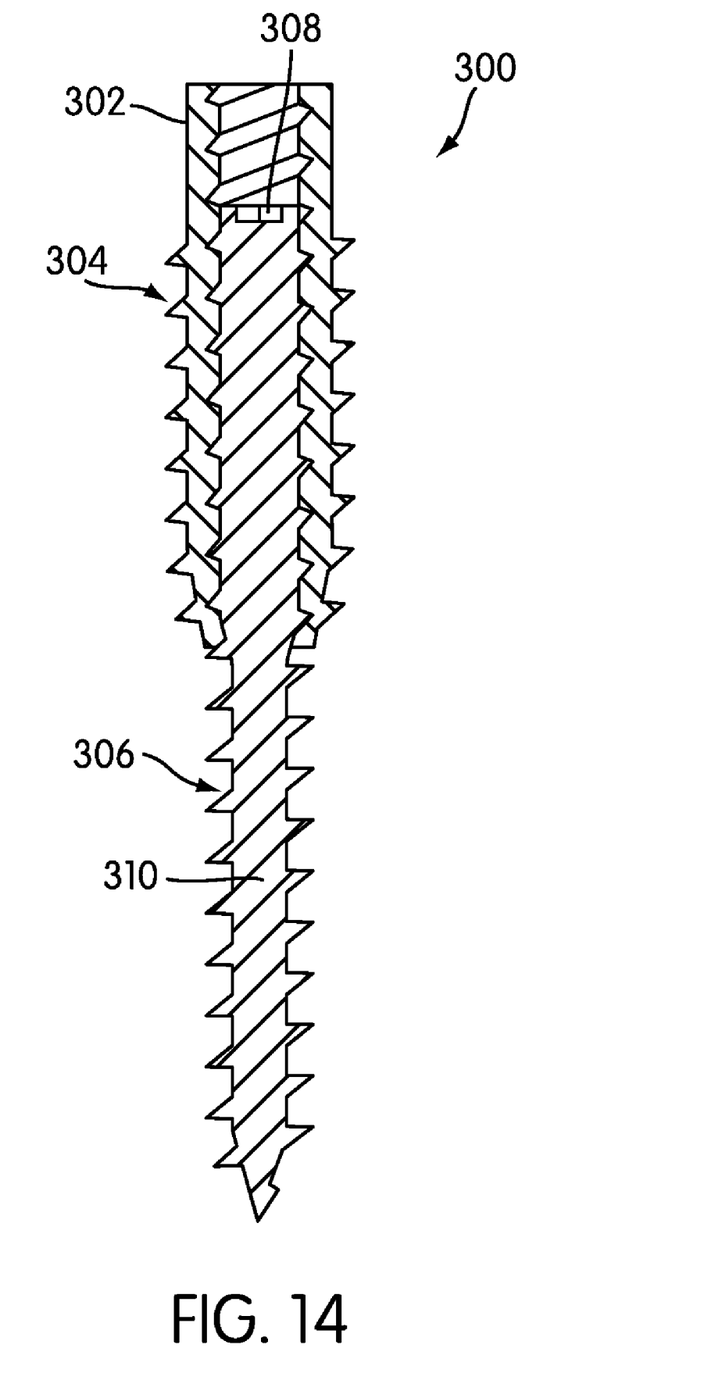
FIG. 14 is a cross-sectional view of an orthopedic screw system according to another embodiment of the invention, illustrating an outer screw with engaging head structure.

In the description above, the head structure that is constructed and adapted to engage orthopedic hardware is described as being on the inner screw 14, 200. However, in some embodiments, that engaging head structure may be provided on the outer member, instead of the inner screw. FIG. 14 is a cross-sectional view similar to the view of FIG. 3, illustrating an embodiment of an orthopedic screw system 300 in which the engaging head structure 302 is provided on the outer member 304. With the engaging head structure 302 on the outer member 304, the inner screw 306 is provided with a socket 308 in the upper end of its shaft 310 to allow the inner screw 306 to be driven. The socket 308 is shaped and sized for a driving tool, and may have any shape and features to allow it to engage a driving tool. For example, the socket 308 may be configured for a hex driver, a Torx driver, a Phillips driver or a slotted driver, among others. One advantage of this configuration is that if the outer member 304 is given the overall diameter of a conventional pedicle or bone screw, then including the engaging head structure 302 on the outer member 304 may help to ensure compatibility with existing orthopedic hardware designed for use with conventional pedicle or bone screw.

Any embodiment of the orthopedic screw system or its components may be surface modified or otherwise modified for the environment of the body. For example, some bone screws are surface treated with hydroxyapatite, and in some embodiments, the components of the orthopedic screw system may be treated with hydroxyapatite. In some embodiments, the components may also be grit blasted or modified in some other way to encourage bone growth.

While the invention has been described with respect to certain exemplary embodiments, the description is intended to be illuminating, rather than limiting. Modifications and changes may be made within the scope of the invention, which is described by the claims.

What is claimed is:

1. An orthopedic screw system, comprising:
an elongate, rigid outer member, the outer member having an exterior sidewall, a first end, a second end opposite the first end, and a longitudinal inner channel of constant diameter that extends between and is open at the first and second ends, the inner channel defining an interior sidewall, the exterior and interior sidewalls of the outer member being provided with screw threads, the screw threads of the exterior sidewall being adapted to engage bone; and
an elongate inner screw having a shaft with a first shaft end and a second shaft end opposite the first shaft end, the shaft including screw threads along substantially the entirety of its length constructed and adapted to engage the screw threads of the interior sidewall of the outer member so as to bring the outer member and the inner screw into engagement;
wherein the outer member and the inner screw are sized and proportioned relative to one another such that in an operative position, at least about 30% of the length of the inner screw extends beyond the second end of the outer member when the inner screw and the outer member are fully engaged with one another; and
wherein the outer member and inner screw are constructed and arranged to be brought into engagement with one another by advancing the inner screw into the first end of the outer member and through the inner channel such that the second shaft end emerges from the second end of the outer member.

2. The orthopedic screw system of claim 1, wherein the orthopedic screw system is a pedicle screw system.

3. The orthopedic screw system of claim 1, wherein the first end of the inner screw shaft is adapted to be positioned proximate to the first end of the outer member when the inner screw and the outer member are fully engaged with one another, and wherein the shaft of the inner screw decreases to a smaller diameter from the first shaft end toward the second shaft end.

4. The orthopedic screw system of claim 3, wherein the screw threads of the inner screw increase in width from the first shaft end toward the second shaft end, such that the inner screw as a whole maintains a constant diameter as the shaft of the inner screw tapers to a smaller diameter from the first shaft end toward the second shaft end.

5. The orthopedic screw system of claim 1, wherein the outer member tapers to a smaller diameter from the first end of the outer member toward the second end of the outer member.

6. The orthopedic screw system of claim 1, wherein about 30% to about 60% of the length of the inner screw extends beyond the second end of the outer member when the inner screw and the outer member are fully engaged with one another.

7. The orthopedic screw system of claim 1, wherein the screw threads of the inner screw have a first screw thread pitch proximate to the first shaft end and a second screw thread pitch proximate to the second shaft end.

8. The orthopedic screw system of claim 7, wherein the second screw thread pitch is coarser than the first screw thread pitch.

9. The orthopedic screw system of claim 1, wherein the outer member is generally cylindrical, and the inner channel is generally cylindrical.

10. The orthopedic screw system of claim 1, wherein the first end and the second end of the outer member are generally parallel to one another.

11. The orthopedic screw system of claim 1, wherein the inner screw or the outer member further comprises a head constructed and adapted to secure an orthopedic implant.

12. A pedicle screw system, comprising:
a generally cylindrical, rigid outer member having
a first end,
a second end, and
an exterior circumferential surface with a set of outer screw threads formed thereon, the set of outer screw threads being constructed and arranged to engage at least a portion of the pedicle of a vertebra so as to secure the outer member in a fixed position within the pedicle of the vertebra oriented such that the second end of the outer member is oriented toward the vertebral body of the vertebra,
the outer member also having a generally longitudinal, generally cylindrical inner channel of constant diameter defined therein, the inner channel extending between and being open at the first and second ends and having inner screw threads formed on an inner circumferential surface of the channel, the inner channel having sufficient diameter to act as a passageway for surgical instruments;
an elongate inner screw, the inner screw having a shaft with a first shaft end, a second shaft end opposite the first shaft end, and screw threads formed on the exterior of the shaft, the screw threads on the shaft being constructed and arranged to engage with the inner screw threads of the outer member so as to bring the inner screw into engagement with the outer member when the inner screw is within the inner channel of the outer member;
wherein the outer member and the inner screw are sized and proportioned relative to one another such that when they are in an operative position with the inner screw within the channel of the outer member, at least 30% of the length of the inner screw extends beyond the second end of the outer member when the outer member and the inner screw are fully engaged with one another and, with the outer member in the fixed position within the pedicle of the vertebra, at least the inner screw extends into the vertebral body of the vertebra; and
wherein the outer member and inner screw are constructed and arranged to be brought into engagement with one another by advancing the inner screw into the first end of the outer member and through the inner channel such that the second shaft end emerges from the second end of the outer member.

13. The pedicle screw system of claim 12, wherein the diameter of the inner screw decreases from the first shaft end toward the second shaft end.

14. The pedicle screw system of claim 13, wherein the screw threads increase in width from the first shaft end toward the second shaft end, such that the inner screw as a whole maintains a constant diameter from the first end to the second end.

15. The pedicle screw system of claim 12, wherein about 30% to about 60% of the length of the inner screw extends beyond the second end of the outer member when the inner screw and the outer member are fully engaged with one another.

16. The pedicle screw system of claim 12, wherein the outer member tapers from its first end toward its second end.

17. The pedicle screw system of claim 12, wherein the screw threads of the inner channel extend substantially the entirety of the length of the inner channel, such that when the inner screw and outer member are in operative engagement, they are engaged over substantially the entirety of the length of the inner channel.

18. An orthopedic screw system, comprising:
an elongate, rigid outer member, the outer member having an exterior sidewall, a first end, a second end opposite the first end, and a longitudinal inner channel of constant diameter that extends between and is open at the first and second ends, the inner channel defining an interior sidewall, the exterior and interior sidewalls of the outer member being provided with screw threads, the screw threads of the exterior sidewall being adapted to engage bone, the outer diameter of the outer member decreasing from the first end toward the second end; and
an elongate inner screw having a head and a shaft with a first shaft end proximate to the head and a second shaft end opposite the first shaft end, the shaft including screw threads constructed and adapted to engage the screw threads of the interior sidewall of the outer member so as to bring the outer member and the inner screw into engagement, the screw threads of the shaft increasing in width from the first shaft end toward the second shaft end;
wherein the outer member and the inner screw are sized and proportioned relative to one another such that in an operative position, at least a portion of the length of the inner screw extends beyond the second end of the outer member when the inner screw and the outer member are fully engaged with one another; and
wherein the outer member and inner screw are constructed and arranged to be brought into engagement with one another by advancing the inner screw into the first end of the outer member and through the inner channel such that the second shaft end emerges from the second end of the outer member.

19. The orthopedic screw system of claim 18, wherein the diameter of the shaft decreases from the first shaft end toward the second shaft end.

20. The orthopedic screw system of claim 19, wherein with the diameter of the shaft decreasing from the first shaft end toward the second shaft end and the width of the shaft screw threads increasing from the first shaft end toward the second shaft end, the inner screw as a whole maintains a constant diameter.

21. The orthopedic screw system of claim 18, wherein an outer diameter of the outer member decreases from the first end toward the second end.

22. The orthopedic screw system of claim 18, wherein at least about 30% of the length of the inner screw extends beyond the second end of the outer member when the inner screw and the outer member are fully engaged with one another.

23. The orthopedic screw system of claim 18, wherein about 30% to about 60% of the length of the inner screw extends beyond the second end of the outer member when the inner screw and the outer member are fully engaged with one another.

24. The orthopedic screw system of claim 18, wherein the length of the outer member is about 50% of the length of the inner screw.

25. An orthopedic screw system, comprising:

an elongate, rigid outer member, the outer member having an exterior sidewall, a first end, a second end opposite the first end, and a longitudinal inner channel of constant diameter that extends between and is open at the first and second ends, the inner channel defining an interior sidewall, the exterior and interior sidewalls of the outer member being provided with screw threads, the screw threads of the exterior sidewall being adapted to engage bone; and an elongate inner screw having a head and a shaft with a first shaft end proximate to the head and a second shaft end opposite the first shaft end, the shaft including screw threads along substantially the entirety of its length constructed and adapted to engage the screw threads of the interior sidewall of the outer member so as to bring the outer member and the inner screw into engagement, the inner screw having a constant diameter at the screw threads such that the inner screw can be advanced into the first end of the outer member and through the inner channel such that the second shaft end emerges from the second end of the outer member;

wherein the outer member and the inner screw are sized and proportioned relative to one another such that in an operative position, at least about 30% of the length of the inner screw extends beyond the second end of the outer member when the inner screw and the outer member are fully engaged with one another.

26. The orthopedic screw system of claim 25, wherein the head of the inner screw comprises a ball.

27. The orthopedic screw system of claim 25, wherein the head of the inner screw comprises a variable angle head.

28. The orthopedic screw system of claim 25, wherein the diameter of the shaft decreases from the first end toward the second end of the shaft.

29. The orthopedic screw system of claim 28, wherein with the diameter of the shaft decreasing from the first shaft end toward the second shaft end and the width of the shaft screw threads increasing from the first shaft end toward the second shaft end, the inner screw as a whole maintains a constant diameter.

* * * * *